United States Patent
Berg et al.

[11] Patent Number: 6,074,416
[45] Date of Patent: Jun. 13, 2000

[54] WIRE CONNECTOR STRUCTURES FOR TUBULAR GRAFTS

[75] Inventors: Todd Allen Berg, Lino Lakes; Paul J. Hindrichs, Plymouth, both of Minn.

[73] Assignee: St. Jude Medical Cardiovascular Group, Inc., Minneapolis, Minn.

[21] Appl. No.: 08/946,742

[22] Filed: Oct. 9, 1997

[51] Int. Cl.[7] .................................................. A61F 2/06
[52] U.S. Cl. ................................................. 623/1; 623/12
[58] Field of Search ................................. 623/1, 11, 12; 606/195, 153

[56] References Cited

U.S. PATENT DOCUMENTS

| | | | |
|---|---|---|---|
| 4,214,587 | 7/1980 | Sakura, Jr. | 128/334 R |
| 4,418,693 | 12/1983 | LeVeen et al. | 128/303 |
| 4,503,569 | 3/1985 | Dotter | 3/1.4 |
| 4,592,754 | 6/1986 | Gupte et al. | 623/1 |
| 4,617,932 | 10/1986 | Kornberg | 128/334 R |
| 4,665,906 | 5/1987 | Jervis | 128/92 YN |
| 4,787,899 | 11/1988 | Lazarus | 623/1 |
| 5,104,399 | 4/1992 | Lazarus | 623/1 |
| 5,135,467 | 8/1992 | Citron | 600/16 |
| 5,211,658 | 5/1993 | Clouse | 623/1 |
| 5,211,683 | 5/1993 | Maginot | 128/898 |
| 5,234,447 | 8/1993 | Kaster | 606/153 |
| 5,275,622 | 1/1994 | Lazarus et al. | 623/1 |
| 5,304,220 | 4/1994 | Maginot | 623/1 |
| 5,316,023 | 5/1994 | Palmaz et al. | 128/898 |
| 5,354,336 | 10/1994 | Kelman et al. | 623/6 |
| 5,366,462 | 11/1994 | Kaster | 606/153 |
| 5,387,235 | 2/1995 | Chuter | 623/1 |
| 5,397,345 | 3/1995 | Lazarus | 623/1 |
| 5,443,497 | 8/1995 | Venbrux | 623/1 |
| 5,452,733 | 9/1995 | Sterman et al. | 128/898 |
| 5,456,712 | 10/1995 | Maginot | 623/1 |
| 5,456,714 | 10/1995 | Owen | 606/153 |
| 5,486,187 | 1/1996 | Schenck | 606/153 |
| 5,489,295 | 2/1996 | Piplani et al. | 623/1 |
| 5,507,769 | 4/1996 | Marin et al. | 606/198 |
| 5,522,880 | 6/1996 | Barone et al. | 623/1 |
| 5,545,214 | 8/1996 | Stevens | 623/2 |
| 5,676,670 | 10/1997 | Kim | 606/108 |
| 5,695,504 | 12/1997 | Gifford, III et al. | 606/153 |
| 5,707,380 | 1/1998 | Hinchliffe | 606/153 |

FOREIGN PATENT DOCUMENTS

| | | | |
|---|---|---|---|
| 0 712 614 A1 | 5/1996 | European Pat. Off. | A61F 2/06 |
| 2 269 104 | 2/1994 | United Kingdom | A61F 2/06 |
| WO 93/00868 | 1/1993 | WIPO | A61F 2/06 |
| WO 96/22745 | 8/1996 | WIPO | A61F 2/06 |
| WO 97/27898 | 8/1997 | WIPO | A61M 29/00 |

*Primary Examiner*—Michael J. Milano
*Attorney, Agent, or Firm*—Fish & Neave; Robert R. Jackson; G. Victor Treyz

[57] ABSTRACT

Connector structures are provided for attaching elongated flexible tubular grafts to the body organ tubing of a patient. The connector structures are formed from wire. A first set of connector wires may be disposed around the periphery of one end of an elongated flexible tubular graft. A second set can be disposed around the periphery of the elongated flexible tubular graft spaced sufficiently from the first set of connector wires to define a gap. The portion of body organ tubing to which the elongated flexible tubular graft is to be attached is received in the gap and engaged by the first and second sets of connector wires. The wires may be formed in the shape of loops. If desired, hooks may be provided on the ends of the wires. The wires may be curved to accommodate attachment of the graft to tubular body organ tubing. The wires may also be formed in annular shapes. The connector structures may be formed as stand-along ring-shaped connectors. Obliquely-angled connections between grafts and body organ tubing may be made using the connector structures.

18 Claims, 17 Drawing Sheets

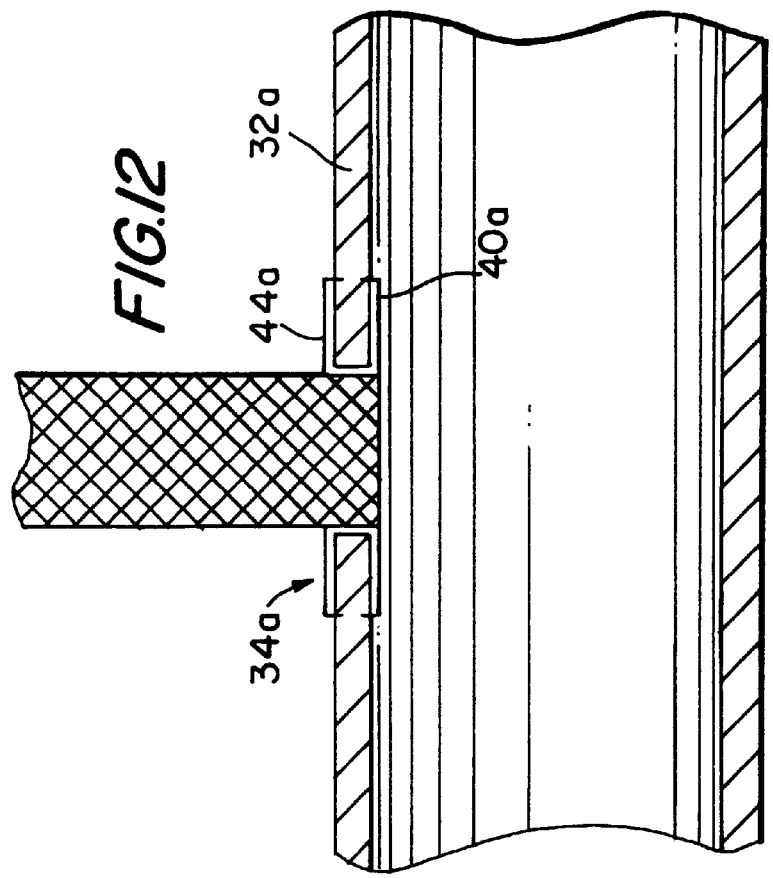
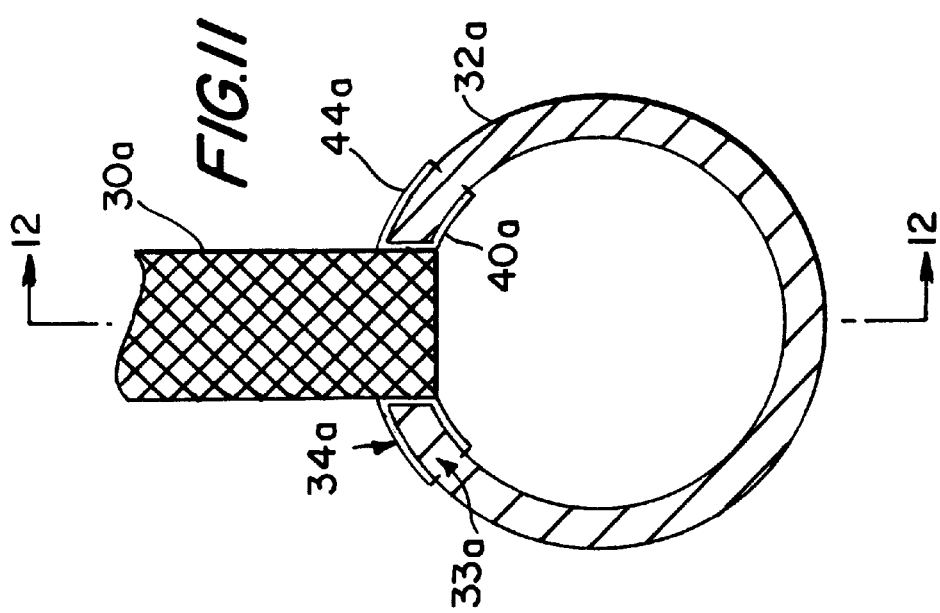

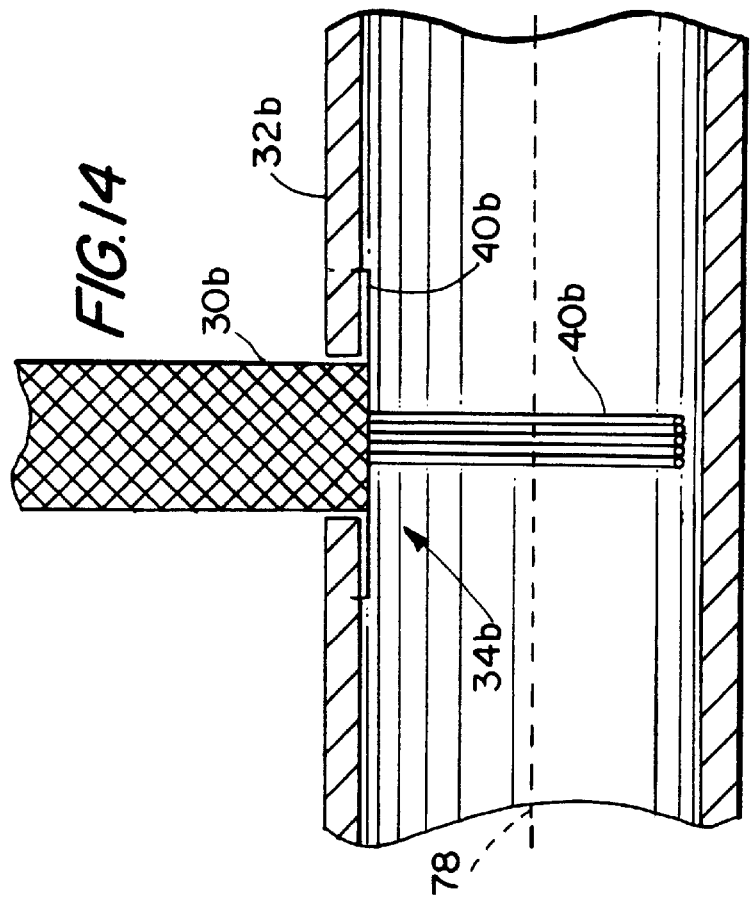
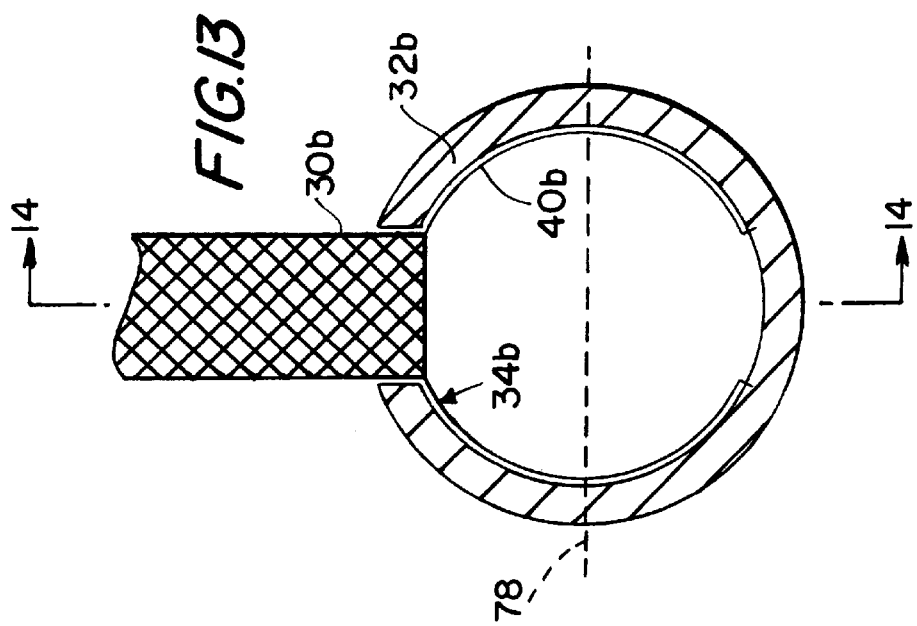

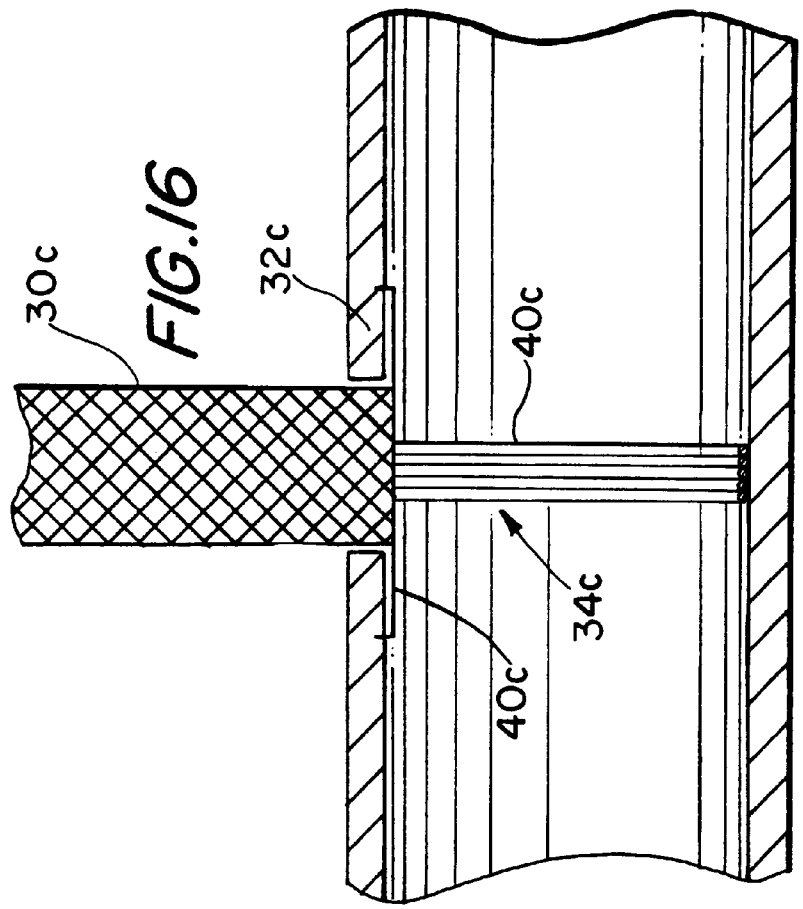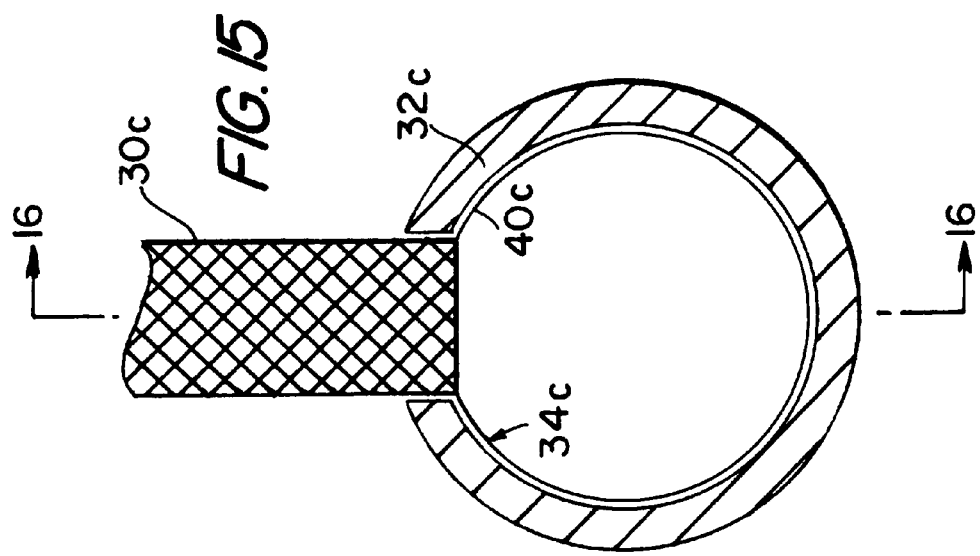

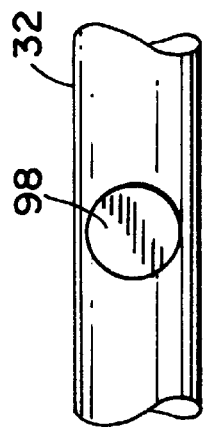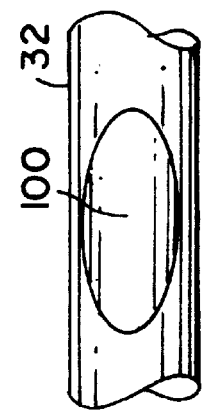
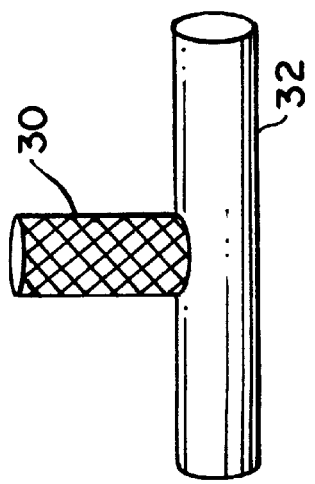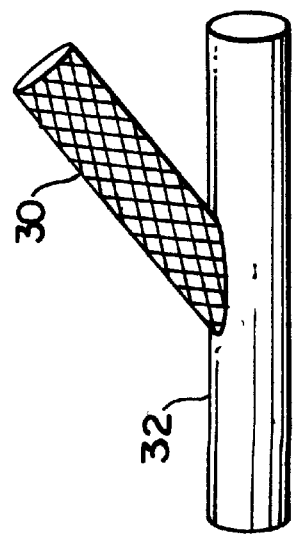

WIRE CONNECTOR STRUCTURES FOR TUBULAR GRAFTS

BACKGROUND OF THE INVENTION

This invention relates to tubular graft structures for replacing or supplementing a patient's natural body organ tubing. More particularly, the invention relates to structures for connecting the ends of such tubular graft structures to body organ tubing.

A patient's weakened or diseased body organ tubing can often be repaired by replacing or supplementing the patient's existing natural body organ tubing with an artificial graft structure. One suitable type of artificial graft structure uses a tubular nitinol mesh frame covered with a silicone coating, as described in Goldsteen et al. U.S. patent application Ser. No. 08/745,618, filed Nov. 7, 1996. Such grafts are highly flexible, so they recover their shape after being stretched. Accordingly, a graft of this type may be stretched axially to reduce its radial dimension and then installed in a patient intraluminally (e.g., through an existing vein or artery). Once delivered to the proper location within the patient, the axially stretched graft may be released, whereupon it expands to regain its original shape.

In addition, flexible artificial grafts may be made distensible like natural body organ tubing to help reduce clot formation when used in vascular applications. Flexible artificial grafts may also be made biocompatible by adjusting their porosity and the composition of their coatings.

Various connector structures may be used to attach flexible artificial grafts to a patient's body organ tubing. For example, a graft may be surgically attached to a patient's body organ tubing with sutures. To install a graft intraluminally, a pronged ring may be expanded from within the end of the graft, thereby piercing the graft and attaching it to surrounding body organ tubing. Barbed flaps and wire hooks may also be used to attach grafts to body organ tubing. Connector structures of these types and other suitable connector structures are described in the above-mentioned Goldsteen et al. U.S. patent application Ser. No. 08/745,618, filed Nov. 7, 1996 and in Bachinski et al. U.S. patent application Ser. No. 08/839,199, filed Apr. 23, 1997.

Although connector structures of these types have various useful features, it would be desirable if connector structures with other features were available.

It is therefore an object of the present invention to provide improved connector structures for attaching grafts to a patient's body organ tubing.

SUMMARY OF THE INVENTION

This and other objects of the invention are accomplished in accordance with the principles of the present invention by providing connectors for attaching flexible graft structures to body organ tubing. The connectors may be entirely or nearly entirely from wire. The flexibility of the wire allows the connectors to be radially contracted during intraluminal insertion into a patient and subsequently radially expanded at the installation site. In addition, the flexibility of the structures makes it possible to match the compliance or flexibility characteristics of the connector with the compliance of the body organ tubing and artificial graft structures at the attachment site.

To form a secure connection between the graft and the body organ tubing, the wire for the connectors can be arranged in two opposing groups of wires near the end of the graft. The wires in the first of the two groups are arranged about he periphery of the end of the graft. The wires in the second group are spaced by a gap from the wires in the first group along the longitudinal axis of the graft The body organ tubing is held in the gap by the two opposing groups of wires.

The wires in the connectors may be loops or may be individual wires. The wires may also be curved to accommodate connections between grafts and natural body organ tubing that is tubular in shape.

If desired, the connectors may be used to form non-right-angle connections between grafts and body organ tubing.

The connectors may also be annular in shape. Such annular connectors may be formed by molding a heat-sensitive wire mesh over an appropriate mandrel and heat treating the wire.

Further features of the invention, its nature and various advantages will be more apparent from the accompanying drawings and the following detailed description of the preferred embodiments.

BRIEF DESCRIPTION OF THE DRAWINGS

FIGS. 6a, 6b, 6c, and 6d are perspective views of illustrative hook structures for use with the connectors of the present invention.

FIG. 11 is an end sectional view of an illustrative connector arrangement in accordance with the present invention in which the connector wires are curved to accommodate the curvature of the tubular body organ tubing to which the graft is connected.

FIG. 12 is a sectional view taken along the line 12—12 in FIG. 11.

FIG. 13 is an end sectional view of another illustrative connector arrangement in accordance with the present invention in which the connector wires are curved to accommodate the curvature of the tubular body organ tubing to which the graft is connected.

FIG. 14 is a sectional view taken along the line 14—14 in FIG. 13.

FIG. 15 is an end sectional view of still another illustrative connector arrangement in accordance with the present invention in which the connector wires are curved to accommodate the curvature of the tubular body organ tubing to which the graft is connected.

FIG. 16 is a sectional view taken along the line 16—16 in FIG. 15.

FIGS. 19a and 19c are side and top views, respectively, of an illustrative right-angle connection between a graft and a length of body organ tubing in accordance with the present invention.

FIGS. 20a and 20b are side and top views, respectively, of an illustrative non-right-angle connection between a graft and a length of body organ tubing in accordance with the present invention.

DETAILED DESCRIPTION OF THE PREFERRED EMBODIMENTS

Figure 1:
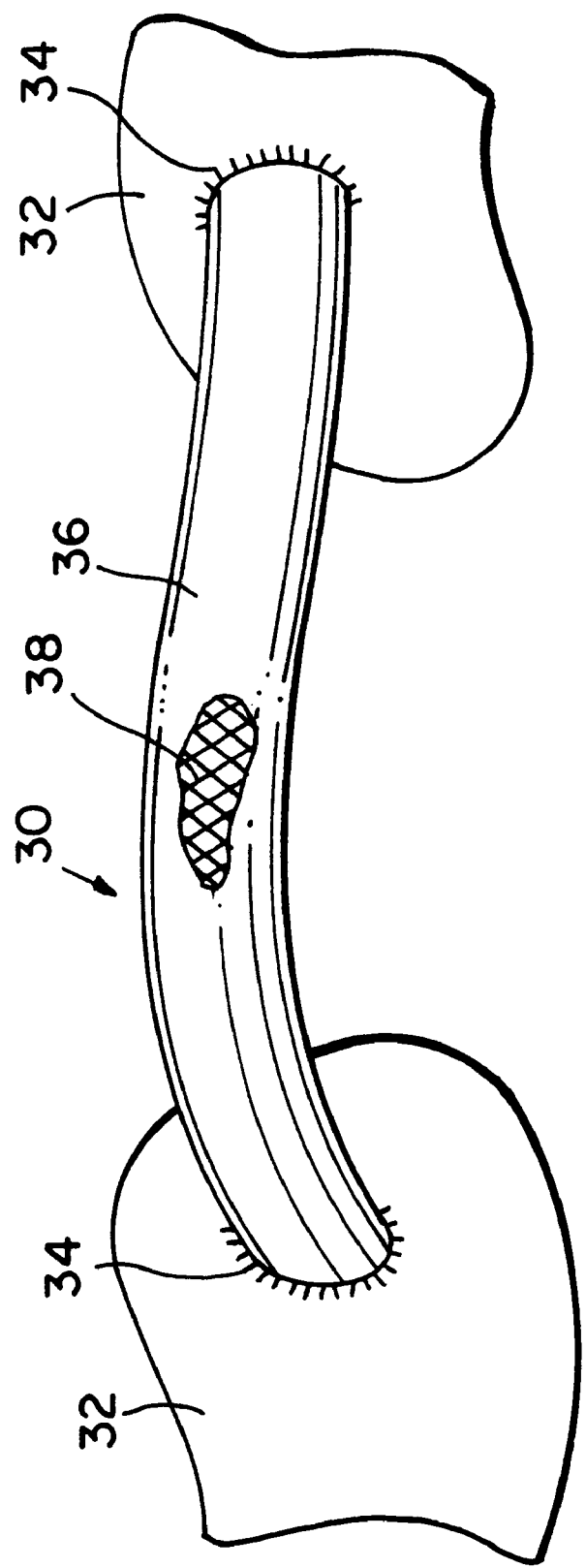
FIG. 1 is a partially cut-away perspective view of an artificial graft structure attached to two sections of body organ tubing with illustrative connectors in accordance with the present invention.

A flexible artificial graft 30 connected to body organ tubing 32 with illustrative wire connectors 34 in accordance with the present invention is shown in FIG. 1. Graft 30 may be a structure formed from a flexible coating 36 covering a frame 38. The preferred materials for forming frame 38 of graft 30 are metals, although polymeric materials may also be used. The presently most preferred material is a braid of nitinol wire. Wire connectors 34 are preferably formed from the same type of flexible material as frame 38 (e.g., nitinol wire). Nitinol wire is heat sensitive, so connectors 34 of various shapes may be formed by bending the wire of a given connector into a desired shape and applying a heat treatment to set the wire in that shape.

Coating 36 is preferably an elastic biocompatible material such as silicone, which fills the apertures formed by the wires in frame 38. Other materials that may be used for coating 36 include polymeric materials such as stretchable urethane, stretchable polytetrafluoroethylene (PTFE), natural rubber, and the like.

If desired, coating 36 can be formed with microscopic pores to help improve biocompatibility. A preferred method of providing a desired porosity is to make coating 36 from an elastic material that is mixed with particles of a material that can be removed (e.g., by vaporization) after coating 36 has been applied to frame 38. When the particles are removed, voids are left in coating 36 that give it porosity.

Graft 30 may be provided with additional coatings such as medicated coatings, hydrophilic coatings, smoothing coatings, collagen coatings, human cell seeding coatings, etc., as described in the abovementioned Goldsteen et al. U.S. patent application Ser. No. 08/745,618, filed Nov. 7, 1996, which is hereby incorporated by reference herein in its entirety. The above-described preferred porosity of coating 12 may help graft 10 to retain these coatings.

In the illustrative example of FIG. 1, graft 30 has been used to form a connection between two sections of body organ tubing 32. Graft 30 may be used to connect portions of body organ tubing of any suitable shape. As defined herein, the term "body organ tubing" generally refers to elongated fluid-containing body organ tissues such as blood vessels and the like and to similar but less elongated body organ tissue structures such as portions of the heart wall. Body organ tubing 32 may be vascular tubing or any other type of body organ tubing.

In accordance with the present invention, connector structures such as wire connectors 34 are used to attach the ends of graft 30 to body organ tubing 32. The illustrative connectors 34 of FIG. 1 are relatively short pieces of protruding wire that are welded to frame 38.

Figure 2:
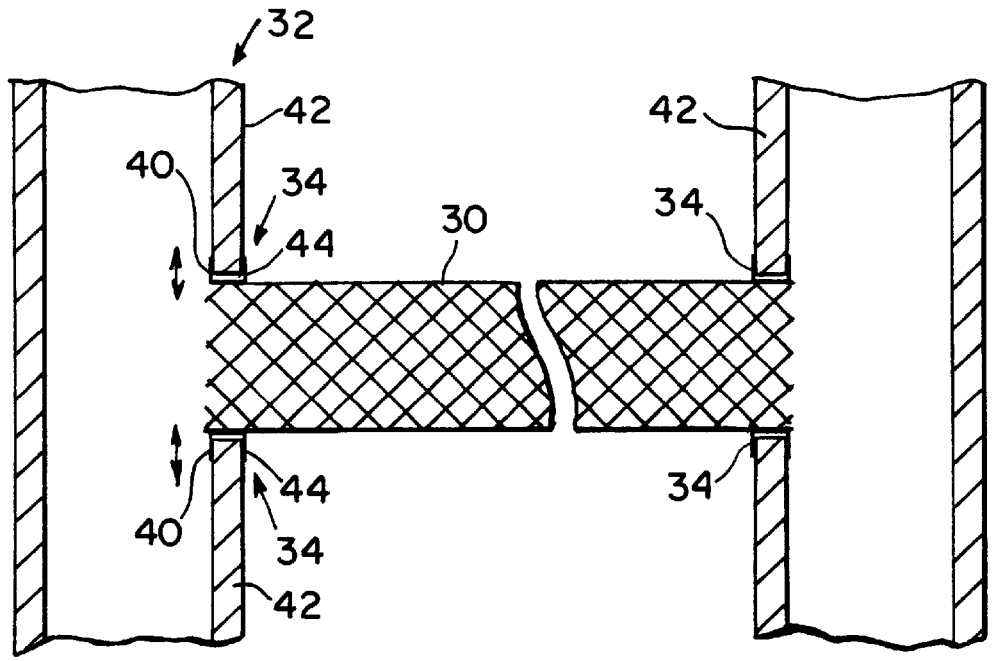
FIG. 2 is a partly-sectional side view of an illustrative graft having wire connectors that are engaging a portion of body organ tubing in accordance with the present invention.

As shown in FIG. 2, portions of the wire forming connectors 34 protrude on both sides of the body organ tubing 32 to which graft 30 is attached. In particular, connector wires 40 protrude on one side of body organ tubing wall 42 (inside tubing 32) and connector wires 44 protrude on the other side of body organ tubing wall 42 (outside tubing 32). This arrangement holds graft 30 firmly in place at the attachment site.

Graft 30 is depicted as a bare metal mesh in FIG. 2 and many of the other FIGS. to show the details of construction of the connector structures. However, graft 30 preferably has a coating such as coating 36 of FIG. 1.

As shown in FIG. 2, wires 40 and 44 in each connector structure 34 are preferably the bent ends of a single piece of wire. If desired, however, connector wires 40 and 44 may be formed from individual wire segments.

Wires 40 and 44 may be approximately 0.1–0.125 inches in length and may be axially spaced to form a gap approximately 0.1 inches wide. For example, wire 40 may be approximately 0.1 inches in length and wire 44 may be approximately 0.125 inches in length. Connectors 34 may be formed from 0.005–0.010 inch diameter round nitinol wire. These dimensions are merely illustrative. Wire of any suitable length and diameter may be used. If desired, the wire in connectors 34 may be coated with a polymeric coating such as polytetrafluoroethylene (PTFE), to reduce abrasion of body organ tubing 32.

Figure 3:
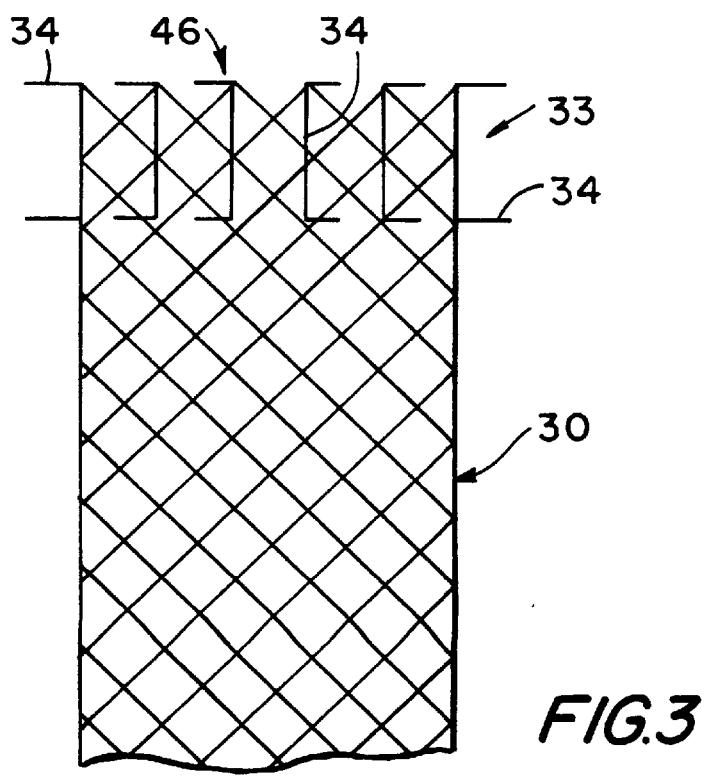
FIG. 3 is a side view of an illustrative graft with wire connectors in accordance with the present invention.

As shown in FIG. 3, connectors 34 are formed around the entire periphery of end 46 of graft 30. The number of connectors 34 that are used depends on the type of graft connection being formed, the difficulty and expense of providing additional connectors 34, and the particular type of connectors 34 that are used. Although connectors 34 are shown at the end of a portion of a graft 30 in FIGS. 1–3, connectors 34 may be placed at an intermediate location along the length of graft 30 if desired. When connectors 34 are used to attach graft 30 to body organ tubing, a portion of the body organ tubing is engaged in gap 33 by connectors 34.

Figure 4A:
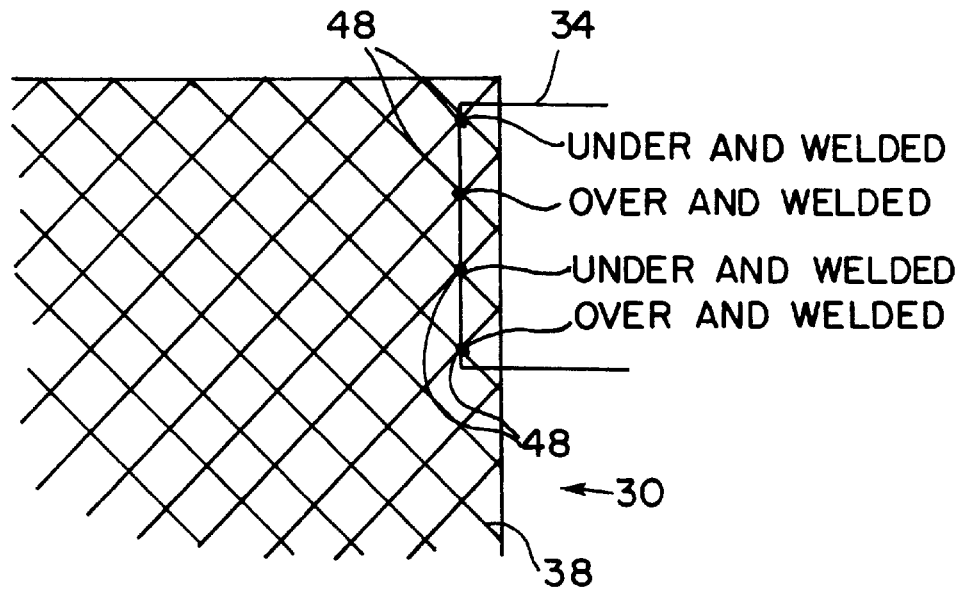
FIGS. 4a and 4b are side views of portions of illustrative grafts having wire connectors that are interwoven and attached to the wire mesh of a graft in accordance with the present invention.

Connectors 34 may be attached to graft 30 using any suitable mounting technique. For example, each connector structure 34 may he interwoven with the pattern of mesh 38 and welded at pic points or wire intersections 48, as shown in FIG. 4a. In the illustrative interweaving pattern shown in FIG. 4a, the wire of connector 34 is first placed under the wires at a wire intersection 48 of frame 38, then over an adjacent wire intersection 48, than under the next adjacent wire intersection 48, then over the next adjacent wire intersection 48.

Figure 4B:
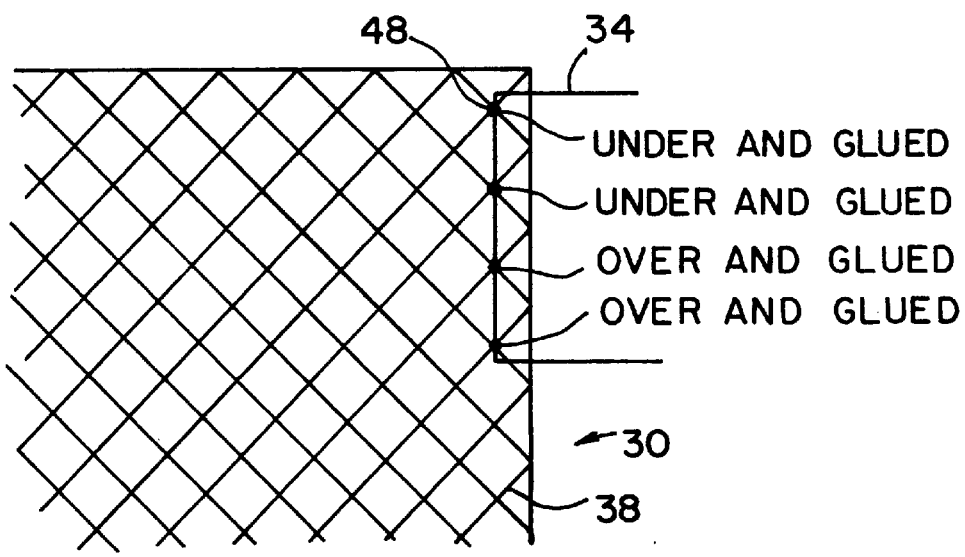

Another illustrative interweaving pattern and mounting technique is shown in FIG. 4b. In FIG. 4b, each connector 34 is glued to frame 38 at a wire intersection 48. The wire of connector 34 is first placed under a wire intersection 48, then under an adjacent wire intersection 48, then over the next adjacent wire intersection 48, then over the next wire intersection 48. Any suitable number of interweaving points and attachment points may be used. The number of times the wire of connector 34 is interwoven with the wire of frame 38 is partly determined by the pic count of frame 38 (i.e., the number of wire intersection points in the mesh of frame 38 per unit length along a straight axial line). The wire of each connector 34 is attached to frame 38 sufficiently often to ensure that connectors 34 are firmly attached to graft 30. Only a few interweaving and attachment points are shown in FIGS. 4a and 4b to avoid over-complicating the drawings.

Figure 5:
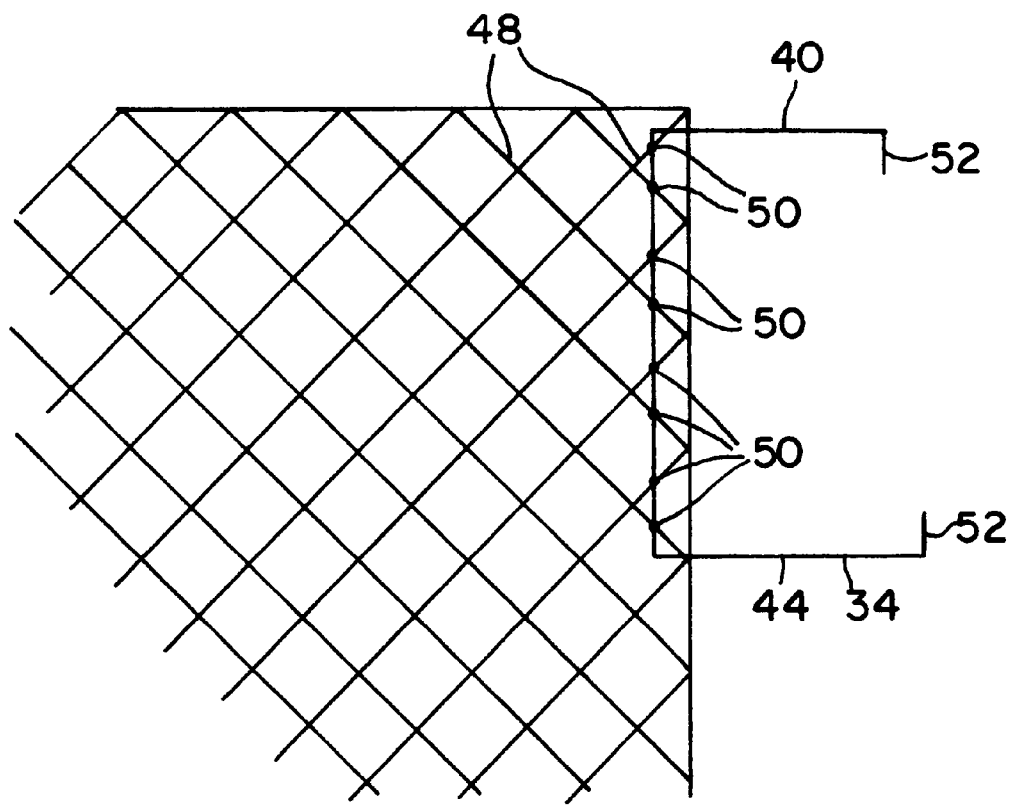
FIG. 5 is a side view of a portion of an illustrative graft having a wire connector attached at points of the mesh other than the wire intersection points of the mesh in accordance with the present invention.

As shown in FIG. 5, connectors 34 may be attached (e.g., welded, glued, or otherwise suitably fastened) at attachment points 50 that do not coincide with wire intersections 48.

FIG. 5 also shows how the ends of wires 40 and 44 of each connector 34 may have hooks 52 that permit connectors 34 to grip body organ tubing 32 (FIG. 1). By gripping body organ tubing 32, hooks 52 facilitate the formation of a farm connection between graft 30 and body organ tubing 32.

Figure 6A:
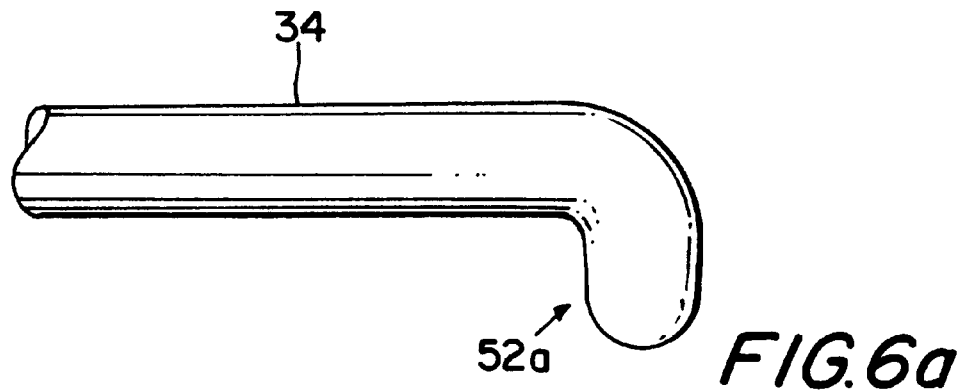
Figure 6B:
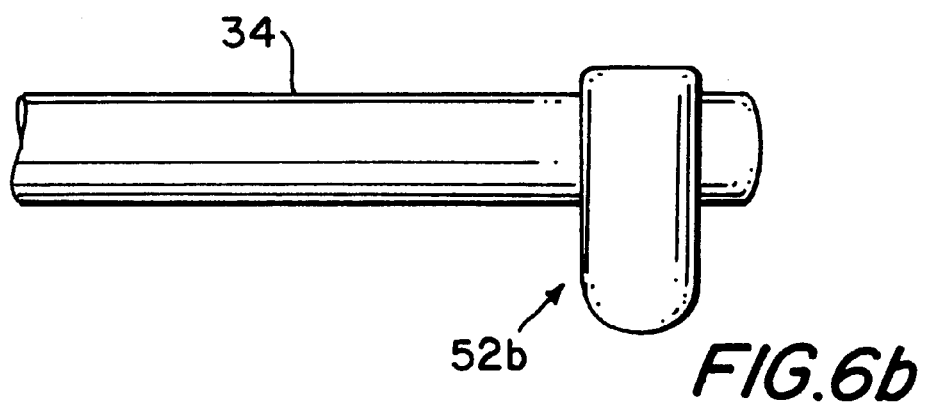
Figure 6C:
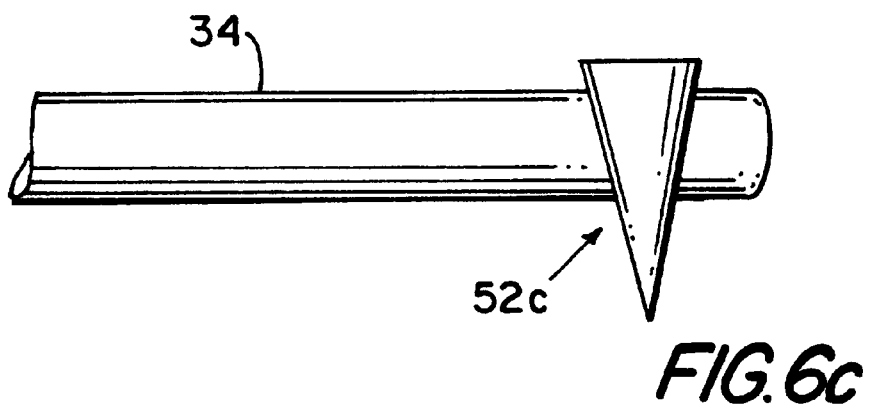

Hooks 52 may be formed by bending the ends of connectors 34, by attaching separate hook members or by any other suitable technique. A hook 52a formed by bending the end of a connector 34 is shown in FIG. 6a. A hook 52b formed by attaching a length of wire to the end of a connector 34 is shown in FIG. 6b. FIG. 6c shows a hook 52c formed by attaching a triangular point to the end of a connector 34. Any portion of a connector that should penetrate body tissue may be barbed as shown, for example, at 52d in FIG. 6d so that the connector resists removal from tissue that it has penetrated.

Figure 7A:
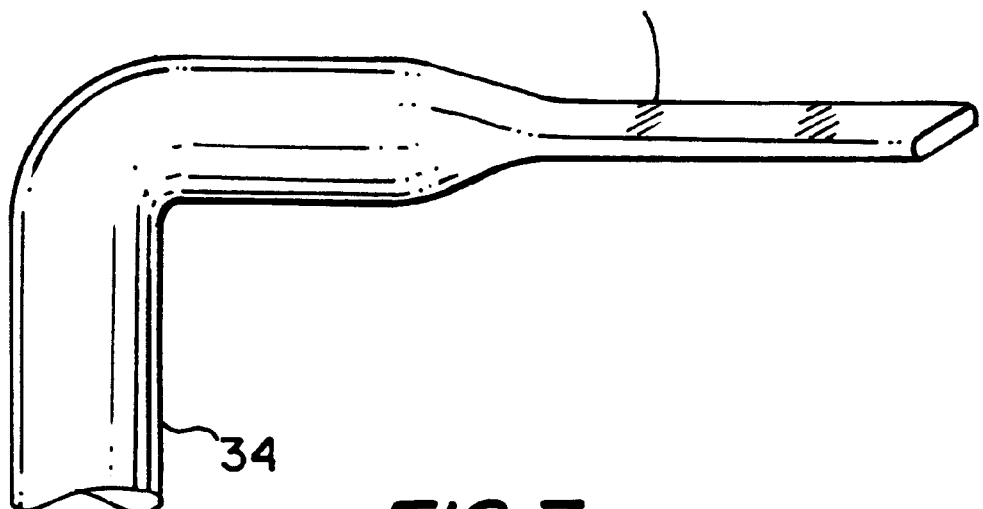
FIG. 7a is a perspective view of an illustrative flattened portion of a wire connector in accordance with the present invention.

In order to reduce tissue abrasion due to the wires of connectors 34 rubbing against body organ tubing 32 (FIG. 1), at least the ends of the wires 40 and 44 of connectors 34 can be flattened rather than being perfectly round, as shown in FIG. 7a. If initially round, wires 40 and 44 (shown as wire 40/44 in FIG. 7a) may be flattened at their ends using any suitable technique.

Figure 7B:
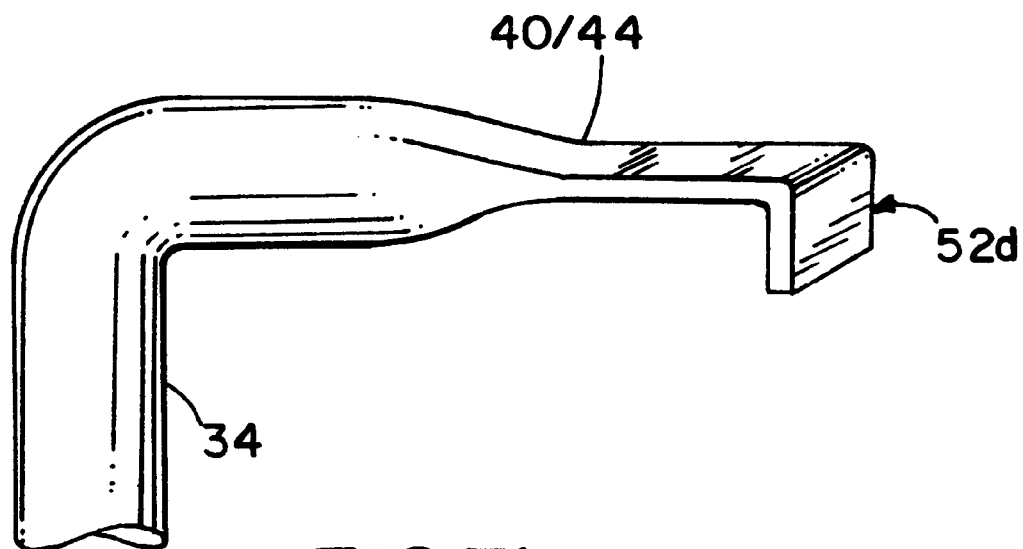
FIG. 7b is a perspective view of an illustrative flattened and hooked portion of a wire connector in accordance with the present invention.

As shown in FIG. 7b, flattened wire 40/44 of connector 34 may be provided with a hook 52d by bending the tip of wire 40/44.

Figure 8:
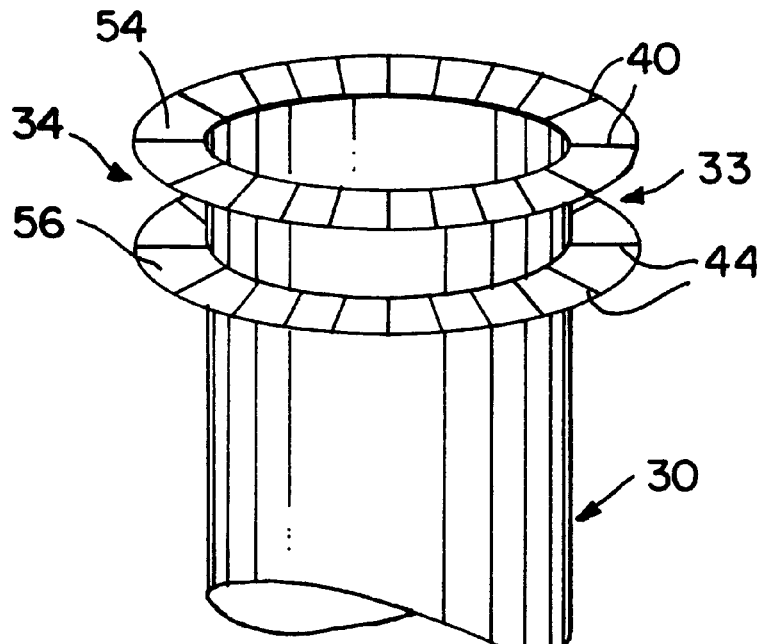
FIG. 8 is a perspective view of an illustrative webbed wire connector structure in accordance with the present invention.

As shown in FIG. 8, wires 40 and 44 of connectors 34 may be provided with webs of elastic material (e.g., silicone), such as webs 54 and 56. Webs 54 and 56 help to shield body organ tubing 32 (FIG. 1) from the potentially abrasive effects of contact with wires 40 and 44 and help to hold graft 30 to the body organ tubing 32 engaged in gap 33.

Figure 9:
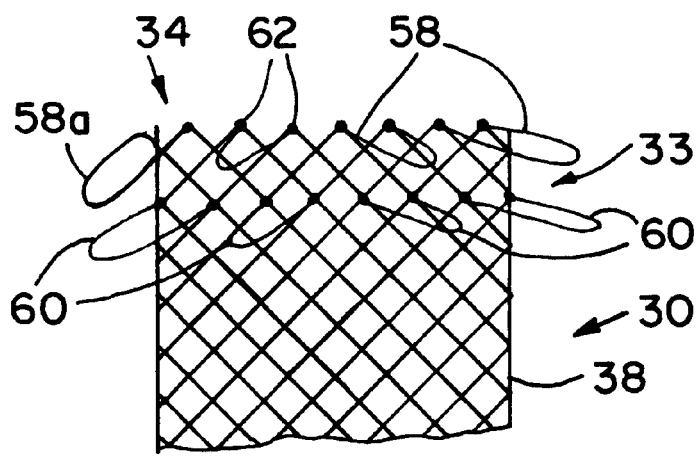
FIG. 9 is a side view of an illustrative graft with looped wire connectors in accordance with the present invention.

If desired, connectors 34 may be formed from wire loops, such as wire loops 58 and 60 shown in FIG. 9. Wire loops 58 and 60 may be formed by bending over extended integrally-formed portions of the wire mesh of graft 30, as illustrated by loop 58a. Alternatively, wire loops 58 and 60 may be formed by attaching wire segments to frame 38 (e.g., by welding, gluing, or other suitable attachment technique) at attachment points 62. If frame 38 is formed from a braided wire having, e.g., 64 strands, particularly suitable configurations for the connector structures of graft 30 may have 32, 16, 8, or 4 loops 58 and 60. When graft 30 of FIG. 9 is connected to body organ tubing, a portion of body organ tubing is engaged in gap 33.

Figure 10A:
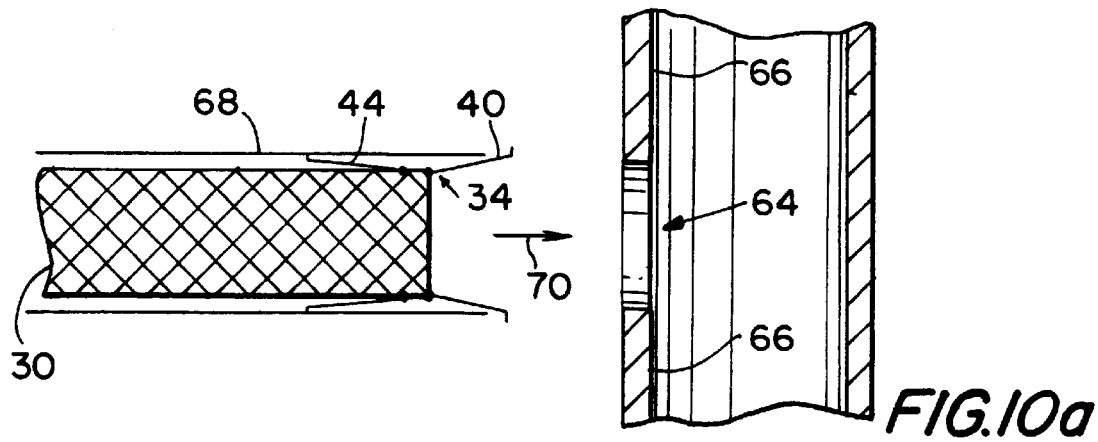
FIGS. 10a, 10b, and 10c are side views of a graft with illustrative connector structures in accordance with the present invention in which the use of a sheath to attach the graft to a portion of body organ tubing is shown.
Figure 10B:
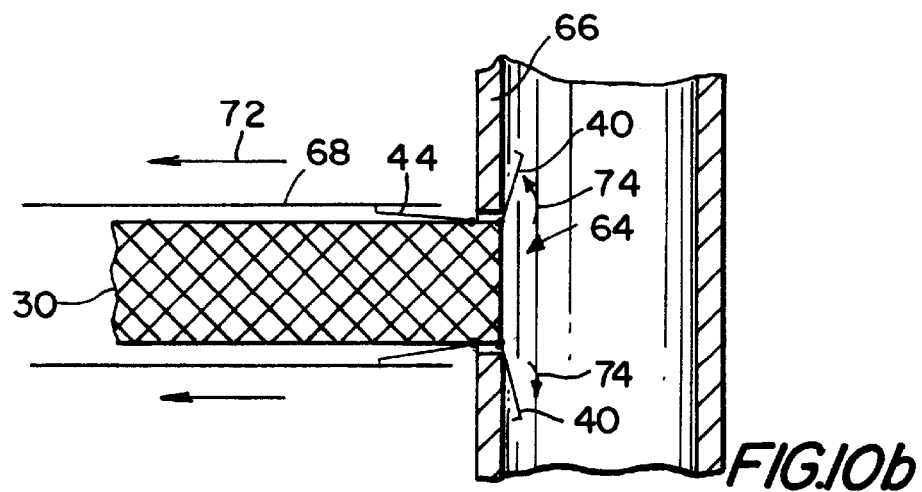
Figure 10C:
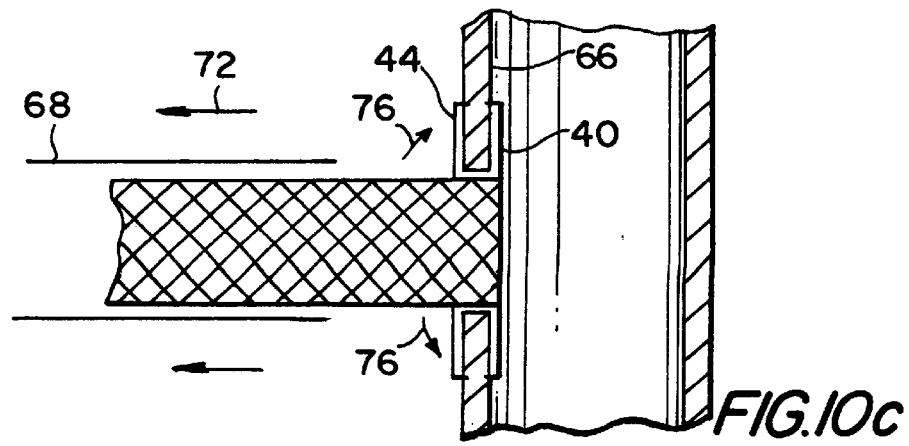

One suitable technique for installing a graft 30 with connectors 34 is shown in FIGS. 10a, 10b, and 10c. Prior to installation, graft 30 is loaded into sheath 68, thereby radially compressing wires 40 and 44, as shown in FIG. 10a. If desired, graft 30 may be delivered to an installation site in a patient intraluminally. At the installation site, graft 30 is inserted into a hole 64 that has been formed in body organ tubing wall 66, as shown in FIG. 10a. During insertion, sheath 68 holds wires 40 and 44 of connectors 34 radially inward and out of the way, so that graft 30 may be advanced through hole 64 in direction 70.

As shown in FIG. 10b, once the distal end of graft 30 is advanced through ho e 64 in body organ tubing wall 66, sheath 68 can be drawn backward in direction 72. Drawing sheath 68 backward releases wires 40, which assume their normal configuration by radially expanding as shown by arrows 74.

As shown in FIG. 10c, sheath 68 is then drawn further backward in direction 72, until wires 44 are released. Wires 44 then assume their normal configuration by radially expanding as shown by arrows 76. Once wires 40 and 44 have assumed their expanded configurations, graft 30 is held in place. Sheath 68 can therefore be removed.

If the other end of graft 30 has connectors 34, the same attachment process may be performed at that end of graft 30 by inserting the preloaded sheath 68 through another hole in the body organ tubing and removing sheath 68 through that hole (rather than moving sheath 68 away from that hole as shown in FIGS. 10a–10c).

Another aspect of the invention is shown in FIGS. 11 and 12. As shown in FIG. 11, graft 30a may be provided with connectors 34a having curved wires 40a and 44a. Wires 40a and 44a are curved to varying degrees to match the curvatures encountered in making a graft connection with a tubular portion of body organ tubing 32a. The end view of FIG. 11 shows how wires 40a and 44b of the connectors 34a that run along the curved portion of tubular body organ tubing 32a are highly curved. The side view of FIG. 12 shows how wires 40a and 44b of the connectors 34a that run along the interior and exterior surfaces of tubular body organ tubing 32a parallel to the longitudinal axis of tubular body organ tubing 32a are not curved. Other connectors 34a that lie in planes not shown in FIGS. 11 and 12 preferably have wires 40a and 44a that are less curved than the wires 40a and 44a of FIG. 11 and that are more curved than the wires 40a and 44a of FIG. 12. Body organ tubing 32a is engaged in the gap 33a between wires 40a and 44a.

As shown in FIGS. 13 and 14, graft 30b may use connectors 34b with wires 40b that extend sufficiently into the interior of tubular body organ tubing 32b that wires like wires 44a of FIG. 11 are not required on the exterior surface of body organ tubing 32b. In particular, because wires 40b run down along the interior surface of tubular body organ tubing 32 past bisecting plane 78, a single set of wires 40b can hold graft 30b in place. The end view of FIG. 13 shows how wires 40b that run along the curved portion of tubular body organ tubing 32b are highly curved. The side view of FIG. 14 shows how wires 40b of the connectors 34b that run along the interior surface of tubular body organ tubing 32b in the axial direction are not curved. Other connectors 34b that lie in planes not shown in FIGS. 13 and 14 may have wires 40b that are less curved than the wires 40b of FIG. 13 and that are more curved than the wires 40b of FIG. 14 if desired.

Another connector arrangement is shown in FIGS. 15 and 16. As shown in FIG. 15, graft 30c may use connectors 34c having some wires 40c that extend completely around the interior of tubular body organ tubing 32c, so that wires such as wires 44a of FIG. 11 are not required on the exterior surface of body organ tubing 32c. In particular, wires 40c in the plane of the end view of FIG. 15 run completely around the interior surface of tubular body organ tubing 32c, so that a single set of wires 40c holds graft 30c in place. The side view of FIG. 16 shows how wires 40c of the connectors 34c that run along the interior surface of tubular body organ tubing 32c parallel to the longitudinal axis of tubular body organ tubing 32c are not curved. Other connectors 34c that lie in planes not shown in FIGS. 15 and 16 may be less curved than the connectors 34c of FIG. 15 and more curved than the connectors 34c of FIG. 16.

The connectors 34a, 34b, and 34c of FIGS. 11–16 may be installed using the installation procedure shown in FIGS. 10a, 10b, and 10c.

Figure 17A:
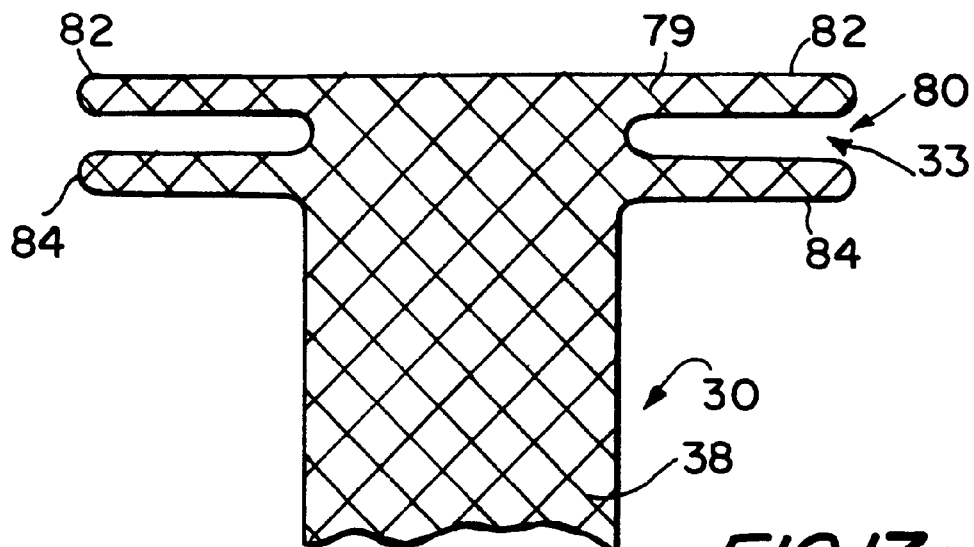
FIGS. 17a and 17b are side views of illustrative annularly-shaped wire connectors in accordance with the present invention.

Another type of wire connector structure that may be used is shown in FIG. 17a. The wires 79 of wire connector 80 are preferably integrally formed from a portion of frame 38 of graft 30. Wire connector 80 has an upper annular portion 82 and a lower annular portion 84. Portions 82 and 84 perform the connecting functions of wires 40 and 44 of connectors such as connectors 34 of FIG. 2. Graft 30 is connected to body organ tubing by engaging a portion of body organ tubing in gap 33 between portions 82 and 84.

One suitable approach for fabricating connector structures such as wire connector 80 is to form frame 38 over a mandrel and then to heat treat frame 38 in a furnace. This technique causes heat sensitive metals such as nitinol to retain the shape of the mandrel after the heat treatment has been completed and the frame 38 has been removed from the mandrel. Similar deformation and heat treatment steps can be used to form connectors 34 of FIGS. 1–16.

Figure 17B:
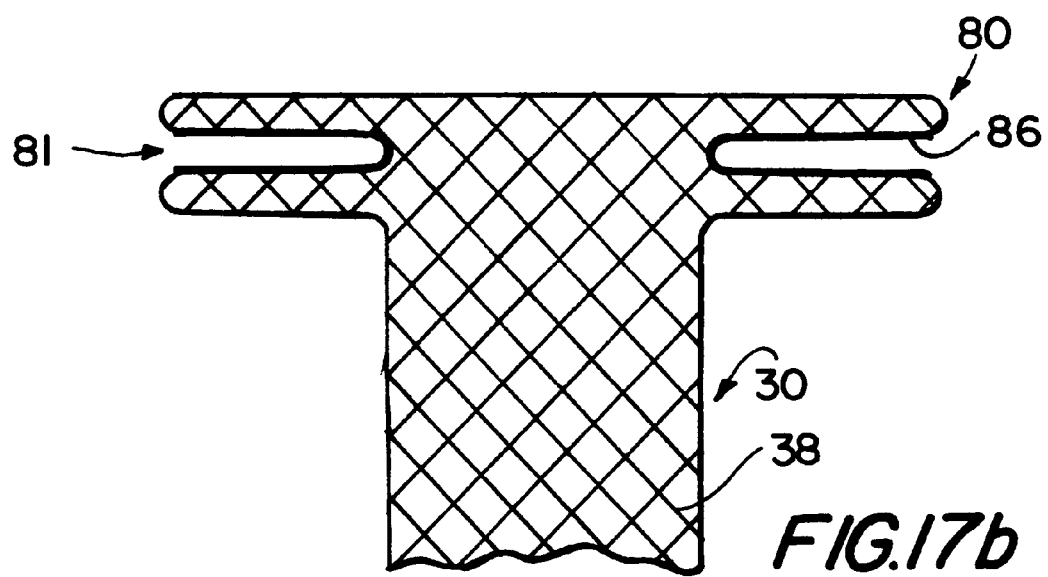

If desired, reinforcing wires 86 may be provided to line the inner surface of connector structure 80 as shown in FIG. 17b. Reinforcing wires 86 may be attached to frame 38 by any suitable attachment technique, such as by welding or gluing.

Figure 18:
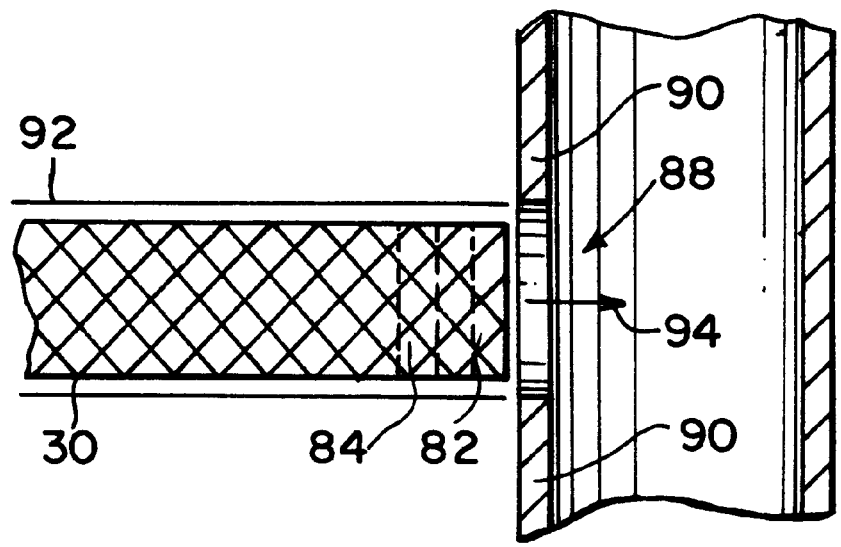
FIGS. 18a and 18b are side views of illustrative steps involved in installing wire connector structures such as the connector structures of FIGS. 17a and 17b.
Figure 18B:
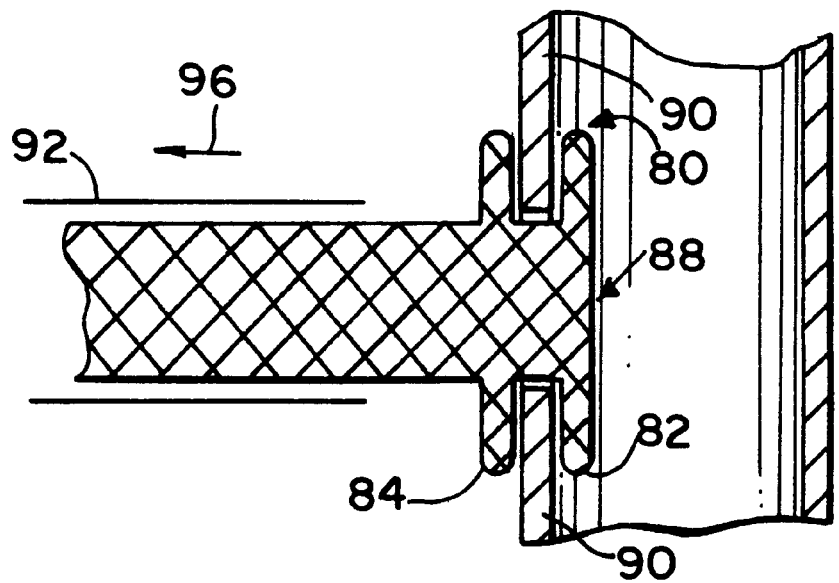

One suitable technique for installing a graft 30 with a connector 80 is shown in FIGS. 18a and 18b. As shown in FIG. 18a, graft 30 is inserted into a hole 88 in body organ tubing wall 90 using sheath 92. Before insertion, graft 30 is preloaded into sheath 92, thereby holding portions 82 and 84 of connector 80 radially inward and out of the way, so that graft 30 may be inserted through hole 88. To insert graft 30 in hole 88 of body organ tubing wall 90, sheath 92 and graft 30 are advanced in direction 94.

As shown in FIG. 18b, once the distal end of graft 30 is advanced through hole 88 in body organ tubing wall 90, sheath 92 can be drawn backward in direction 96. Drawing sheath 92 backward releases portions 82 and 84 of wire connector 80, so that connector 80 assumes its normal radially-expanded configuration and holds graft 30 in place. Sheath 92 can therefore be removed.

If the other end of graft 30 has a connector 80, the same attachment process may be performed at that end of graft 30 by inserting the preloaded sheath 92 through a hole in the body organ tubing near that end and removing sheath 92 through that hole (rather than moving sheath 92 away from the hole as shown in FIG. 18a).

It is sometimes desirable to make connections between a graft and a portion of body organ tubing at a non-right angle, sometimes referred to herein as an oblique angle. The wire and frame-based connectors of the present invention are suitable for forming such connections.

A typical right-angle connection between a graft 30 and a portion of body organ tubing 32 is shown in FIG. 19a. As shown in FIG. 19b, such a right-angle connection creates a circular hole 98 in body organ tubing 32.

An oblique-angle connection between graft 30 and a portion of body organ tubing 32 is shown in FIG. 20a. Making an oblique-angle connection typically forms a hole 100 in body organ tubing 32 that has a larger perimeter than the circular hole 98 of FIG. 19b. The large perimeter of hole 100 provides a larger contact area over which to form a firm connection between graft 30 and body organ tubing 32. In addition, during some installation procedures it may not be convenient or practical to use a right-angle arrangement.

Figure 21:
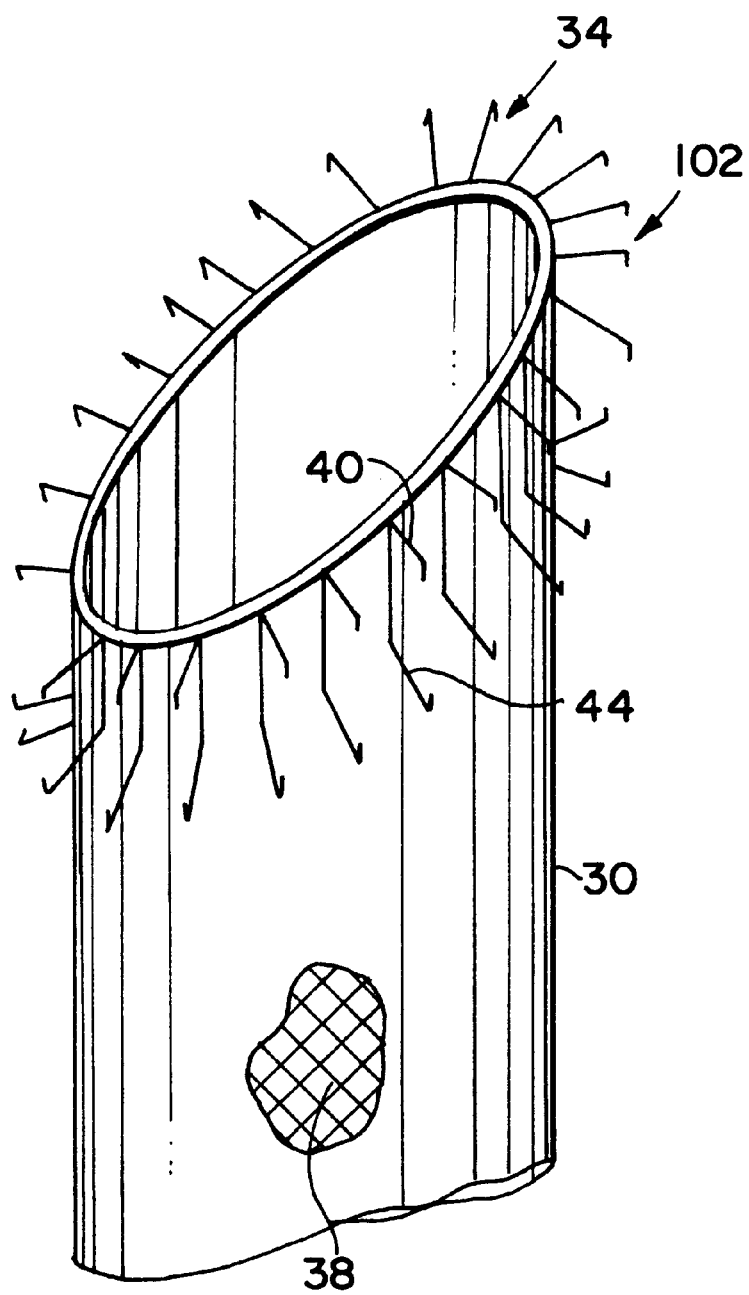
FIG. 21 is a perspective view of a non-right-angled end of a graft having illustrative connectors in accordance with the present invention.
Figure 22:
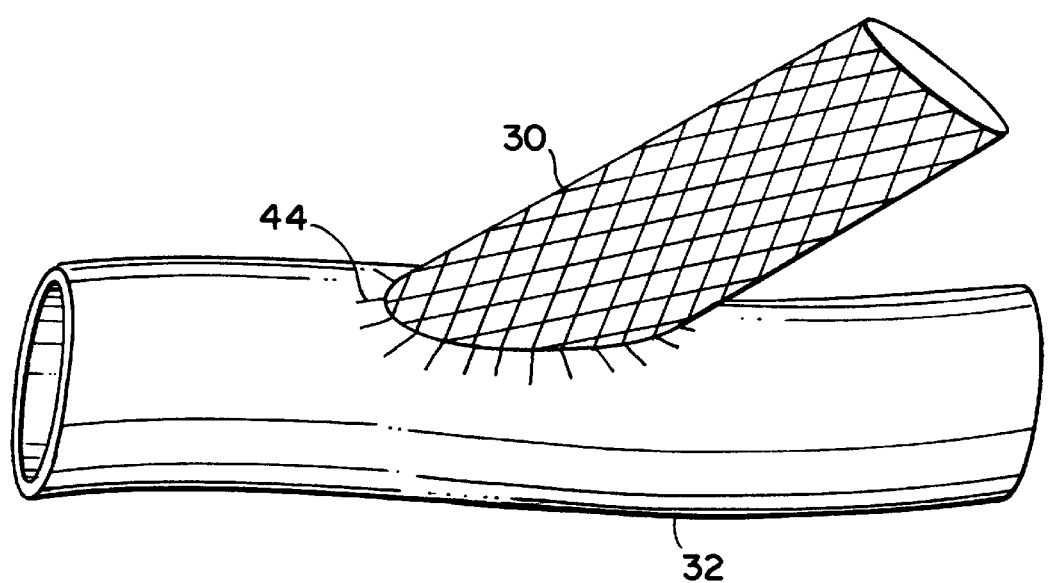
FIG. 22 is a perspective view of the graft of FIG. 21 connected to a length of body organ tubing.

Any of connectors 32 or 80 may be used to form an oblique-angle connection between a graft 30 and a portion of body organ tubing 32. FIG. 21 shows how the obliquely-angled distal tip 102 of graft 30 may have connectors 34 formed from wires 40 and 44 around its periphery. When installed, wires 44 grip the outer surface of body organ tubing 32, as shown in FIG. 22. Wires 40 (not shown in FIG. 22) grip the corresponding inner surface of the body organ tubing 32 of FIG. 22.

The oblique-angle connection between graft 30 and body organ tubing 32 of FIG. 22 uses connectors 34 formed from wires 40 and 44. If desired, similar oblique-angle connections may be formed using the webbed connector arrangement of FIG. 8, the looped connector arrangement of FIG. 9, the curved connector wire arrangements of FIGS. 11–16, or the integral frame connector arrangement of FIGS. 17a and 17b. When used for oblique-angle graft attachment procedures, sheaths such as sheath 68 of FIG. 10 and sheath 92 of FIG. 18 preferably have obliquely-angled ends.

Figure 23:
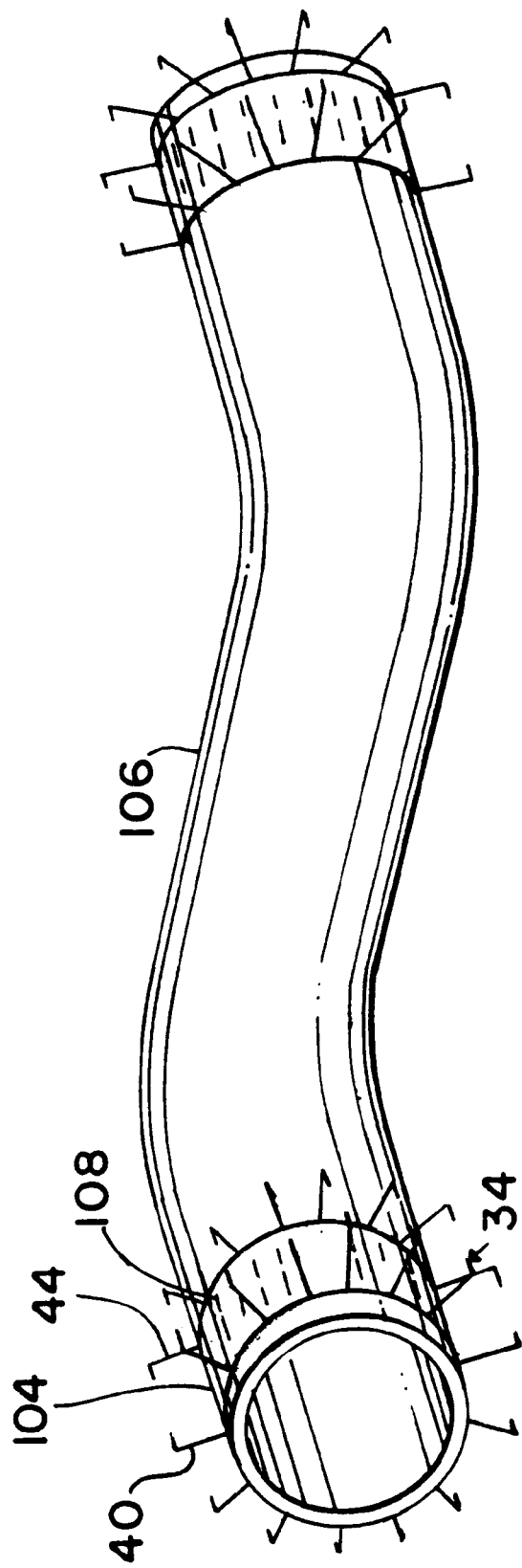
FIG. 23 is a perspective view of a length of natural body tubing to which two illustrative ring-shaped wire connector structures have been attached in accordance with the present invention.

Wire connectors 32 and 80 may be provided as stand-alone connectors if desired. For example, connectors such as connectors 34 of FIG. 2 may be attached to suitable ring structures 104, as shown in FIG. 23. Ring structures 104, which are preferably formed from a suitable elastomeric material, may be attached to a length of natural graft 106 by sutures 108. The resulting natural graft with artificial connectors may be used whenever a natural graft is appropriate but the ease of installation provided by connectors 34 is desired. Similar ring-like stand-alone structures may be provided using the webbed connector arrangement of FIG. 8, the looped connector arrangement of FIG. 9, the curved connector wire arrangements of FIGS. 11–16, or the integral frame connector arrangement of FIGS. 17a and 17b.

It will be understood that the foregoing is only illustrative of the principles of the invention, and that various modifications can be made by those skilled in the art without departing from the scope and spirit of the invention.

The invention claimed is:

1. An artificial graft for attachment to the body organ tubing of a patient comprising:

an elongated flexible tubular graft structure; and
   a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires, wherein:
      at least some of the wires in the first and second pluralities of wires comprise wire loops;

the attached wire loops are attached to the elongated flexible tubular graft structure; and the wire loops are welded to the elongated flexible tubular graft structure.

2. An artificial graft for attachment to the body organ tubing of a patient comprising:

an elongated flexible tubular graft structure;

a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires; and hooks on at least some of the wires in the first and second pluralities of wires for engaging the body organ tubing;

wherein the hooks comprise separate attached hook members.

3. An artificial graft for attachment to the body organ tubing of a patient comprising:

an elongated flexible tubular graft structure;

a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires; and hooks on at least some of the wires in the first and second pluralities of wires for engaging the body organ tubing;

wherein the hooks have barbs.

4. An artificial graft for attachment to the body organ tubing of a patient comprising:

an elongated flexible tubular graft structure; and a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires;

wherein at least some of the wires in the first and second pluralities of wires are welded to the elongated flexible tubular graft structure.

5. An artificial graft for attachment to the body organ tubing of a patient comprising:

an elongated flexible tubular graft structure; and a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires;

wherein at least some of the wires in the first and second pluralities of wires are glued to the elongated flexible tubular graft structure.

6. An artificial graft for attachment to the body organ tubing of a patient comprising:

an elongated flexible tubular graft structure; and a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires, wherein:

the elongated flexible tubular graft structure comprises a wire mesh frame; and at least some of the wires in the first and second pluralities of wires are interwoven with the wire mesh frame.

7. An artificial graft for attachment to the body organ tubing of a patient comprising:

an elongated flexible tubular graft structure; and a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires, wherein:

each wire in the first plurality of wires is associated with one of the wires in the second plurality of wires;

each wire in the first plurality of wires is formed from the same piece of wire as its associated wire in the second plurality of wires;

the elongated flexible tubular graft structure comprises a wire mesh frame having mesh wires that intersect at wire intersection points;

at least some of the wires in the first and second pluralities of wires are interwoven with the wire mesh frame; and at least some of the wires in the first and second pluralities of wires are welded to the elongated flexible tubular graft structure at the wire intersection points.

8. An artificial graft for attachment to the body organ tubing of a patient comprising:

an elongated flexible tubular graft structure;

a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires; and an elastic web covering at least some of the wires in the first and second pluralities of wires.

9. An artificial graft for attachment to the body organ tubing of a patient comprising:

an elongated flexible tubular graft structure; and a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires;

wherein the portion of body organ tubing to which the artificial graft is attached has a hole, the artificial graft structure further comprising a tubular sheath that holds the first and second pluralities of wires in a radially compressed position during insertion of the artificial graft and the tubular sheath into the hole and that releases the first and second pluralities of wires during removal of the tubular sheath while the artificial graft is maintained within the hole so that the first and second pluralities of wires radially expand to engage the portion of body organ tubing.

10. An artificial graft for attachment to the body organ tubing of a patient comprising:

an elongated flexible tubular graft structure; and a first plurality of wires that are disposed around the periphery of one end of the elongated flexible tubular graft structure and a second plurality of wires that are disposed around the periphery of the elongated flexible tubular graft structure at an axially spaced position relative the first plurality of wires to define a gap in which a portion of the body organ tubing is engaged between the first and second pluralities of wires;

wherein the elongated flexible tubular graft structure has an obliquely-angled end.

11. An artificial graft for attachment to a portion of the body organ tubing of a patient, wherein the portion of body organ tubing s tubular in shape and wherein a plane bisecting the tubular body organ tubing lies along the longitudinal axis of the tubular body organ tubing, the artificial graft comprising:

an elongated flexible tubular graft structure; and a plurality of wires disposed around the periphery of one end of the elongated flexible tubular graft structure, wherein at least some of the wires extend away from the end of the elongated flexible tubular graft structure and along the inner surface of the tubular body organ tubing past the bisecting plane.

12. The artificial graft of claim 11, wherein at least some of the wires that extend along the inner surface of the tubular body organ tubing extend entirely around the inner surface of the tubular body organ tubing.

13. An artificial graft for attachment to the body organ tubing of a patient comprising:

an elongated flexible tubular graft structure; and a first plurality of radially extending wires that are disposed around the periphery of one end of the elongated flexible tubular graft structure and a second plurality of radially extending wires that are disposed around the periphery of the elongated flexible tubular graft structure at an axially spaced position relative the first plurality of wires to define a gap which engages a portion of the body organ tubing without piercing the body organ tubing with the wires, wherein at least some of the wires in the first and second pluralities of wires are welded to the elongated flexible tubular graft structure.

14. An artificial graft for attachment to the body organ tubing of a patient comprising:

an elongated flexible tubular graft structure; and a first plurality of radially extending wires that are disposed around the periphery of one end of the elongated flexible tubular graft structure and a second plurality of radially extending wires that are disposed around the periphery of the elongated flexible tubular graft structure at an axially spaced position relative the first plurality of wires to define a gap which engages a portion of the body organ tubing without piercing the body organ tubing with the wires, wherein at least some of the wires in the first and second pluralities of wires are glued to the elongated flexible tubular graft structure.

15. An artificial graft for attachment to the body organ tubing of a patient comprising:

an elongated flexible tubular graft structure; and a first plurality of radially extending wires that are disposed around the periphery of one end of the elongated flexible tubular graft structure and a second plurality of radially extending wires that are disposed around the periphery of the elongated flexible tubular graft structure at an axially spaced position relative the first plurality of wires to define a gap which engages a portion of the body organ tubing without piercing the body organ tubing with the wires, wherein:

the elongated flexible tubular graft structure comprises a wire mesh frame; and at least some of the wires in the first and second pluralities of wires are interwoven with the wire mesh frame.

16. An artificial graft for attachment to the body organ tubing of a patient comprising:

an elongated flexible tubular graft structure; and a first plurality of radially extending wires that are disposed around the periphery of one end of the elongated flexible tubular graft structure and a second plurality of radially extending wires that are disposed around the periphery of the elongated flexible tubular graft structure at an axially spaced position relative the first plurality of wires to define a gap which engages a portion of the body organ tubing without piercing the body organ tubing with the wires, wherein:

each wire in the first plurality of wires is associated with one of the wires in the second plurality of wires;

each wire in the first plurality of wires is formed from the same piece of wire as its associated wire in the second plurality of wires;

the elongated flexible tubular graft structure comprises a wire mesh frame having mesh wires that intersect at wire intersection points;

at least some of the wires in the first and second pluralities of wires are interwoven with the wire mesh frame; and at least some of the wires in the first and second pluralities of wires are welded to the elongated flexible tubular graft structure at the wire intersection points.

17. An artificial graft for attachment to the body organ tubing of a patient comprising:

an elongated flexible tubular graft structure; and a first plurality of radially extending wires that are disposed around the periphery of one end of the elongated flexible tubular graft structure and a second plurality of radially extending wires that are disposed around the periphery of the elongated flexible tubular graft structure at an axially spaced position relative the first plurality of wires to define a gap which engages a portion of the body organ tubing without piercing the body organ tubing with the wires, wherein the portion of body organ tubing to which the artificial graft is attached has a hole, the artificial graft structure further comprising a tubular sheath that holds the first and second pluralities of wires in a radially compressed position during insertion of the artificial graft and the tubular sheath into the hole and that releases the first and second pluralities of wires during removal of the tubular sheath while the artificial graft is maintained within the hole so that the first and second pluralities of wires radially expand to engage the portion of body organ tubing.

18. An artificial graft for attachment to the body organ tubing of a patient comprising:

an elongated flexible tubular graft structure; and a first plurality of radially extending wires that are disposed around the periphery of one end of the elongated flexible tubular graft structure and a second plurality of radially extending wires that are disposed around the periphery of the elongated flexible tubular graft structure at an axially spaced position relative the first plurality of wires to define a gap which engages a portion of the body organ tubing without piercing the body organ tubing with the wires, wherein the elongated flexible tubular graft structure has an obliquely-angled end.

* * * * *

UNITED STATES PATENT AND TRADEMARK OFFICE
CERTIFICATE OF CORRECTION

PATENT NO. : 6,074,416
DATED : June 13, 2000
INVENTOR(S) : Todd Allen Berg et al.

Page 1 of 1

It is certified that error appears in the above-identified patent and that said Letters Patent is hereby corrected as shown below:

<u>Title page,</u>
U.S PATENT DOCUMENTS, change "4,214,587 7/1980" to -- 4,214,587 6/1980 --.

FOREIGN PATENT DOCUMENTS, please add:

```
-- 670 239       1/1994  Australian Pat Off. .......................... A61F  2/06
0 539 237 A1     4/1993  European Pat. Off. ........................... A61F  2/06
0 637 454 A1     2/1995  European Pat. Off. ........................... A61M 25/10
0 680 734 A2     1/1995  European Pat. Off. ........................... A61F  2/06
0 684 022 A2    11/1995  European Pat. Off. ........................... A61F  2/06
WO 96/18361      6/1996  WIPO ......................................... A61F  2/06
WO 97/13463      4/1997  WIPO ......................................... A61B 17/00
WO 97/13471      4/1997  WIPO ..........................................A61B 19/00 --.
```

<u>Column 2,</u>
Line 1, change "he" to -- the --.
Line 3, change "graft" to -- graft. --.

<u>Column 4,</u>
Line 2, change "abovementioned" to -- above-mentioned --.

<u>Column 5,</u>
Line 2, change "than" to -- then --.
Line 27, change "farm" to -- firm --.

<u>Column 6,</u>
Line 15, change "ho e" to -- hole --.

Signed and Sealed this

Eighth Day of January, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,074,416                                          Page 1 of 2
DATED         : June 13, 2000
INVENTOR(S)   : Todd Allen Berg et al.

It is certified that error appears in the above-identified patent and that said Letters Patent is hereby corrected as shown below:

<u>Title page,</u>
Item [57], ABSTRACT,
Line 16, change "stand-along" to -- stand-alone --.

<u>Drawings,</u>
FIG. 18, change "FIG. 18" to -- FIG. 18a --.

<u>Column 2,</u>
Line 40, change "6c, and 6d" to -- and 6c --.

<u>Column 3,</u>
Line 19, change "19c" to -- 19b --.

<u>Column 4,</u>
Line 6, change "12 may help graft 10" to -- 36 may help graft 30 --.

<u>Column 5,</u>
Line 37, delete "as shown, for example, at".
Line 38, delete "52d in FIG. 6d".

<u>Column 6,</u>
Lines 38 and 41, change "44b" to -- 44a --.

<u>Column 7,</u>
Line 64, change "FIG. 18a" to -- FIGS. 18a and 18b --.

UNITED STATES PATENT AND TRADEMARK OFFICE
CERTIFICATE OF CORRECTION

PATENT NO.    : 6,074,416
DATED         : June 13, 2000
INVENTOR(S)   : Todd Allen Berg et al.

It is certified that error appears in the above-identified patent and that said Letters Patent is hereby corrected as shown below:

<u>Column 8,</u>
Line 34, change FIG. 18" to -- FIG. 18a --.

Signed and Sealed this

Fourteenth Day of January, 2003

JAMES E. ROGAN
*Director of the United States Patent and Trademark Office*